US00PP27425P2

(12) United States Plant Patent
Johnson, Jr.

(10) Patent No.: US PP27,425 P2
(45) Date of Patent: Nov. 29, 2016

(54) ***MAHONIA* HYBRID PLANT NAMED 'MARVEL'**

(50) Latin Name: *Mahonia×media*
Varietal Denomination: Marvel

(71) Applicant: Ozzie W. Johnson, Jr., Marietta, GA (US)

(72) Inventor: Ozzie W. Johnson, Jr., Marietta, GA (US)

(73) Assignee: ITSAUL PLANTS LLC, Alpharetta, GA (US)

( * ) Notice: Subject to any disclaimer, the term of this patent is extended or adjusted under 35 U.S.C. 154(b) by 86 days.

(21) Appl. No.: 14/545,141

(22) Filed: Mar. 30, 2015

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Penny J. Aguirre

(57) ABSTRACT

A new cultivar of hybrid *Mahonia×media*, 'Marvel', that is characterized by its unique leaflets with smooth margins, terminating in a single spine at the apex, its leaves arranged in a whorl around the stem with a tight rosette displayed at the terminus, its upright plant habit, its large inflorescence composed of racemes of small, fragrant yellow flowers that bloom from late fall to mid winter in Georgia, and its berries that are blue-green in color when young and begin to ripen in February to a deep blue-purple color.

3 Drawing Sheets

Botanical classification: *Mahonia×media.*
Variety denomination: 'Marvel'.

BACKGROUND OF THE INVENTION

The present invention relates to a new and distinct cultivar of *Mahonia*, botanically known as *Mahonia×media* 'Marvel', and will be referred to hereafter by its cultivar name, 'Marvel'. 'Marvel' is an evergreen shrub grown for use as a landscape plant.

The Inventor discovered 'Marvel' in 2005 as a chance seedling in his garden in Marietta, Ga. The new cultivar is believed to have derived from the open pollination of *Mahonia×media* 'Charity' (not patented) as the female parent as the seedling was found under a rooted cutting of 'Charity'. The male parentage is unknown.

Asexual propagation of the new cultivar was first accomplished by the Inventor using softwood tip cuttings in 2007 in Marietta, Ga. Asexual propagation by softwood tip and hardwood stem cuttings and tissue culture has determined that the characteristics of the new cultivar are stable and are reproduced true to type in successive generations.

SUMMARY OF THE INVENTION

The following traits have been repeatedly observed and represent the characteristics of 'Marvel'. These attributes in combination distinguish 'Marvel' as a unique cultivar of *Mahonia×media.*

1. 'Marvel' exhibits leaflets with spineless and entire margins, terminating in a single spine at the apex.
2. 'Marvel' exhibits leaves arranged in a whorl around the stem with a tight rosette at the terminus.
3. 'Marvel' exhibits a rosette of racemes of small, moderately fragrant, yellow flowers that bloom from late fall through mid winter in Georgia.

4. 'Marvel' exhibits berries that are blue-green in color when young ripen February to April to a deep blue-purple color.
5. 'Marvel' exhibits an upright plant habit.

'Charity', the presumed female parent of 'Marvel', is similar to 'Marvel' in having an evergreen, upright plant habit and in having moderately fragrant flowers. 'Charity' differs from 'Marvel' in having spines present on leaflet margins. 'Marvel' can also be compared to the *Mahonia×media* cultivars, 'Winter Sun' (not patented), 'Buckland' (not patented), and 'Lionel Fortescue' (not patented). 'Winter Sun', 'Buckland', and 'Lionel Fortescue' are similar to 'Marvel' in having an evergreen plant habit and in blooming in late fall with fragrant yellow flowers. 'Winter Sun', 'Buckland', and 'Lionel Fortescue' all differ from 'Marvel' most significantly in having spines present on the leaflet margins.

BRIEF DESCRIPTION OF THE DRAWINGS

The accompanying colored photographs illustrate the overall appearance and distinct characteristics of the new *Mahonia.*

The photographs in FIG. 1 and FIG. 2 were taken of plants about 2 years in age as grown outdoors in a 2-gallon container in partial shade in Alpharetta, Ga.

Figure 3:
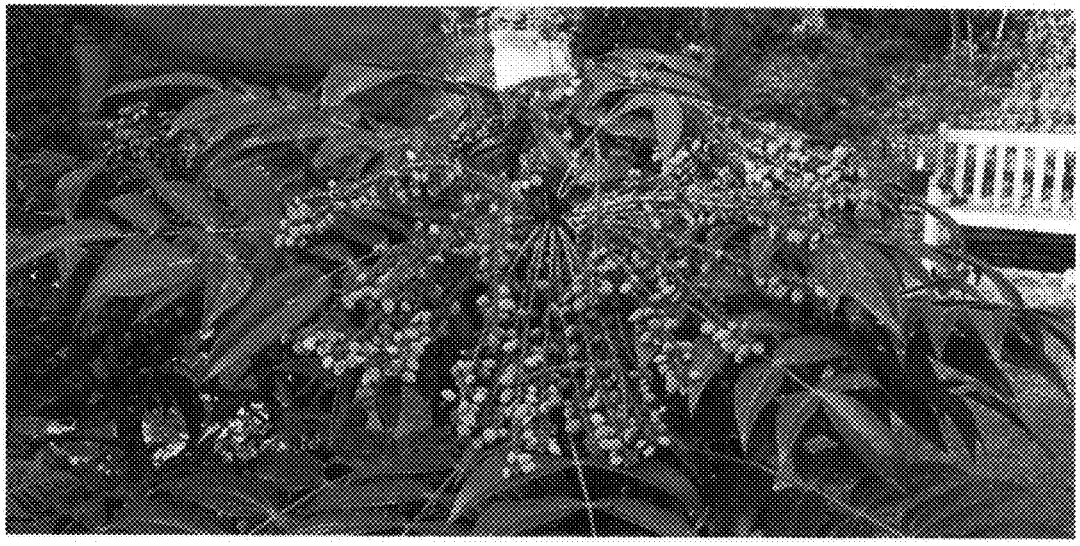
Figure 4:
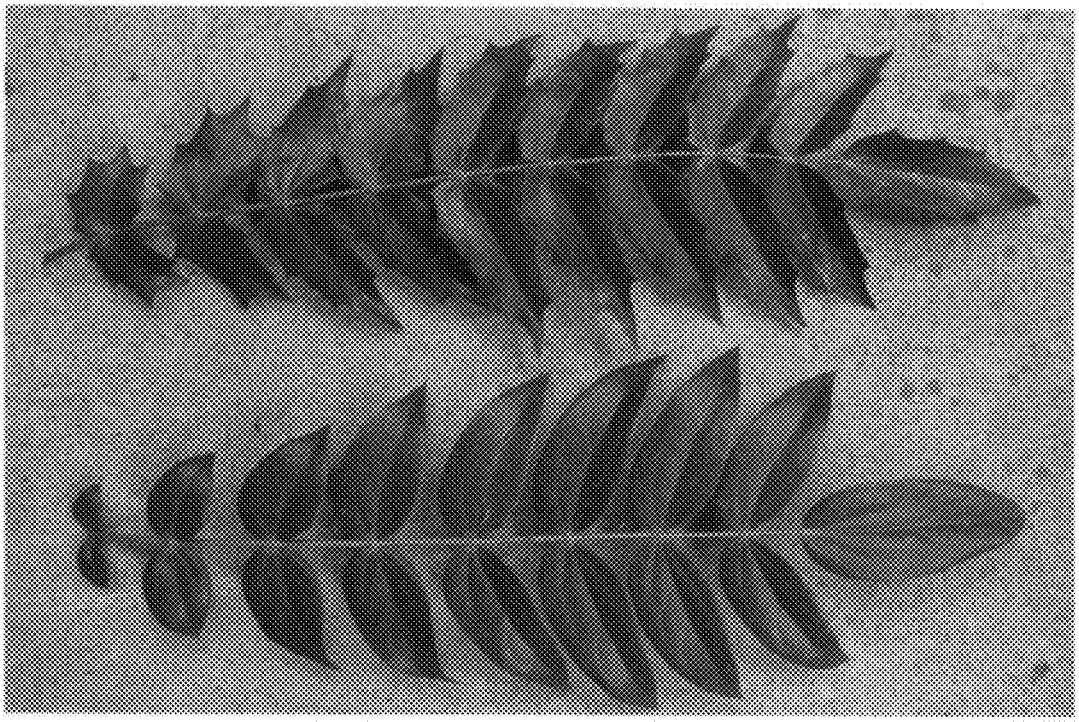

The photographs in FIG. 3 and FIG. 4 were taken of a 3 year-old plant as grown in a garden in Marietta, Ga.

Figure 1:
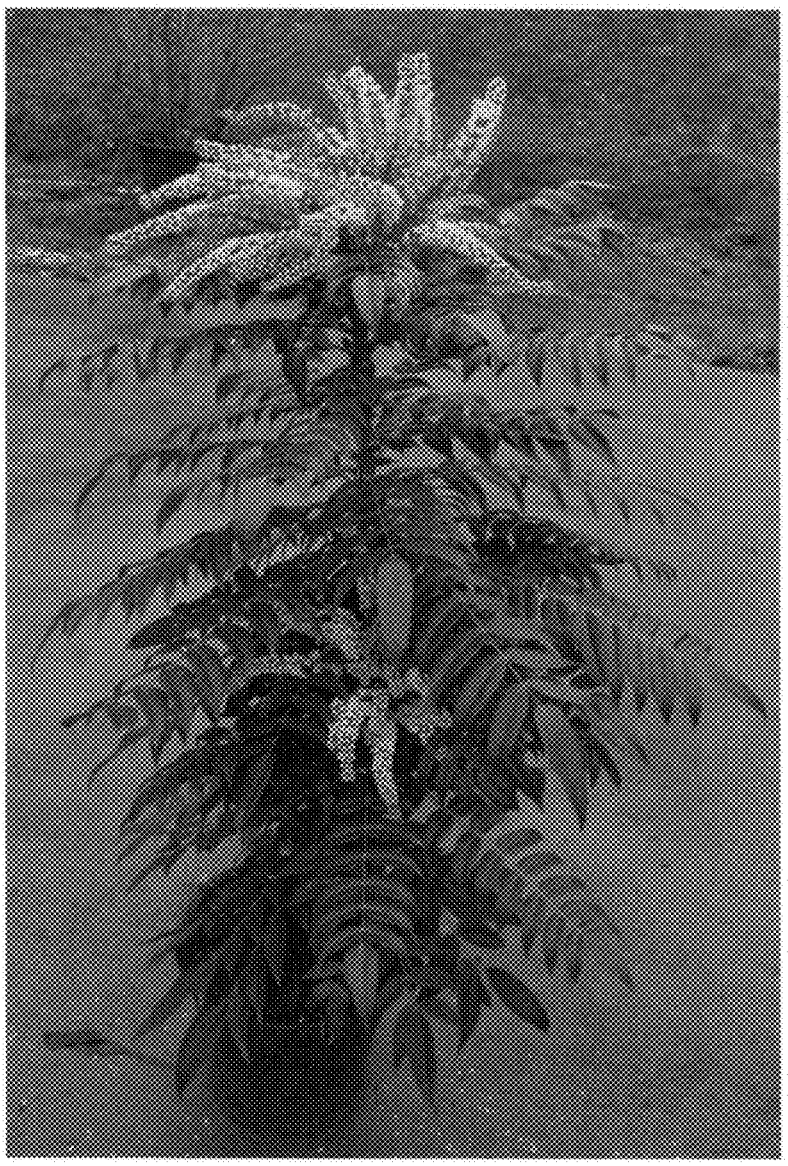

The photograph in FIG. 1 provides a side view of 'Marvel' in bloom.

Figure 2:
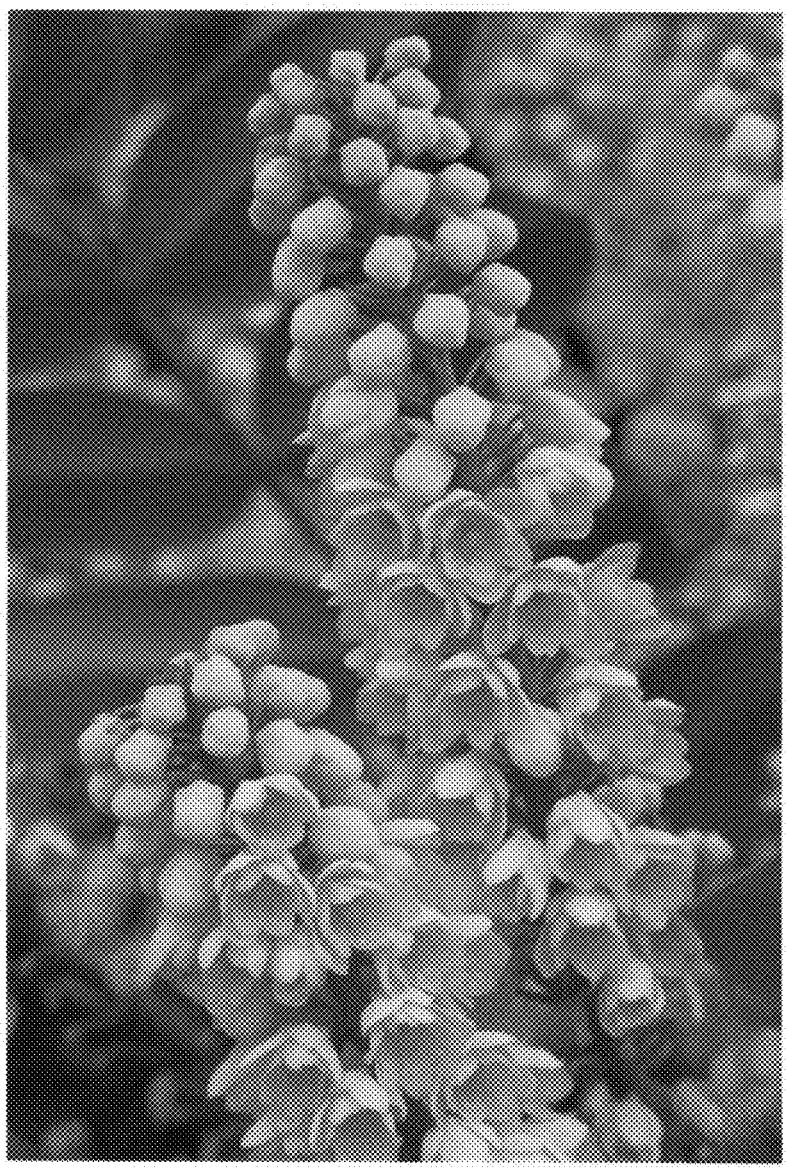

The photograph in FIG. 2 provides a close-up view of the flower racemes of 'Marvel'.

The photograph in FIG. 3 provides a view of the berries of 'Marvel'.

The photograph in FIG. 4 provides a comparison between a leaf of 'Charity' (top) and 'Marvel' (bottom).

The colors in the photographs are as close as possible with the digital photography techniques available, the color values cited in the detailed botanical description accurately describe the colors of the new *Mahonia*.

DETAILED BOTANICAL DESCRIPTION

The following is a detailed description of a three year-old plant of the new cultivar as grown outdoors in partial shade in Alpharetta, Ga. in a 5-gallon container. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for an average of 8 to 12 weeks beginning in November in Georgia.

*Plant type.*—Evergreen shrub.

*Plant habit.*—Upright.

*Height and spread.*—Mature height is unknown, a three year-old plant as grown in a 5-gallon container reaches an average of 100 cm in height and 50 cm in width.

*Cold hardiness.*—At least in U.S.D.A. Zone 7.

*Diseases and pests.*—No disease or insect pests have been observed on crops of 'Marvel' under any cultural or environmental conditions presented.

*Root description.*—Fleshy.

*Propagation*—Softwood tip cuttings (preferred), hardwood stem cuttings and tissue culture.

*Growth rate.*—Moderate.

*Root development.*—Roots initiate in 4 to 6 weeks and fully develop in a 5×7 cm container in 8 to 12 weeks.

Stem description:

*Shape.*—Round, robust.

*Stem color.*—New growth emerges a blend of 144A and 144B, becoming a blend of 161A, 199A and 199B as it becoming scaly, mature bark is a blend of 199D and N200D.

*Stem size.*—An average of 80 cm in length and 2.7 cm in diameter.

*Stem surface.*—New growth; glabrous and semi-glossy, becomes scaly and finally bark with vertical fissures and segments.

*Branching.*—Sparse initially, naturally begins at around 2 years in age without pruning, tip pruning generally promotes the formation of 2 new branches just below the cut, an average of 5 to 6 branches at 3 years in age with a branch angle of 20° to vertical.

Foliage description:

*Leaf shape.*—Oblanceolate in outline.

*Leaf division.*—Imparipinnate (odd-pinnate).

*Leaf base.*—Broadly attenuate.

*Leaf apex.*—Acute.

*Leaf fragrance.*—None.

*Leaf arrangement.*—Whorls, leaflets opposite.

*Leaf attachment.*—Petiolate.

*Leaf size.*—Average of 29 cm in length and 10 cm in width.

*Leaf quantity.*—An average of 25 leaves per stem 58 cm in length.

*Leaflet shape.*—Broadly lanceolate with leaflets near base ovate.

*Leaflet apex.*—Acute with spine about 3 mm in length and <1 mm in width.

*Leaflet base.*—Rounded.

*Leaflet venation.*—Not prominent, main veins tri-nerved, 144A on upper surface and 144B on lower surface.

*Leaflet margins.*—Entire, smooth, lacking spines.

*Leaflet surface.*—Glabrous and semi-glossy on upper surface, glabrous and lustrous to slightly glaucous on lower surface.

*Leaflet size.*—An average of 6.5 cm in length and 3 cm in width.

*Leaflet internode length.*—An average of 2.5 cm.

*Leaflet quantity.*—An average of 19 per leaf 30 cm in length.

*Leaf color.*—Newly expanded leaves; upper surface 137A, lower surface 146D, mature leaves; upper surface 146A and becoming 147A, lower surface 146D becoming 147C.

*Petioles.*—About 1.5 cm in length and 1.5 mm in width (at base), sheathed around stem at ligule, a blend of 146B and 144A in color, glabrous and semi-glossy surface, one pair of leaves at apex; ovate in shape, an average of 2 cm in length and 1.5 cm in width, other characteristics similar to leaflets.

*Rachis.*—Round, an average of 27 cm in length and 3 mm in diameter, surface is glabrous and lustrous, color on young leaves; 144A, color on mature leaves; 146B.

*Ligules.*—Membranous, 1 mm in width, 146B in color.

Inflorescence description:

*Inflorescence type.*—Fascicles of racemes arranged in whorls emerging above leaf whorls, racemes open from bottom of raceme towards apex, racemes of tightly packed cup-shaped flowers.

*Inflorescence size.*—Racemes average 18 to 20 cm (including base of peduncle) in length and about 2.5 cm in diameter, overall width approximates two-thirds the width of the terminal foliage rosette.

*Flower buds.*—Oblong-globose in shape, up to 6 mm in length and 4 mm in width prior to opening, emerging 151C and becoming 8A in color prior to opening.

*Flower fragrance.*—Mild daffodil-like scent.

*Lastingness of inflorescence.*—4 to 6 weeks from the opening of the lower flowers to the opening of the upper flowers of the raceme, individual flowers persist for an average of 1 to 2 days.

*Flower quantity.*—About 85 flowers per raceme, about 16 racemes per whorl, new whorls emerge just below foliar rosette for duration of flowering season.

*Flower type.*—Perfect, campanulate.

*Flower aspect.*—Outward facing on raceme, racemes are held at about a 10° to 30° angle from the stem.

*Flower size.*—Average of 7 mm in diameter and 6 mm in depth.

*Peduncles.*—Average 18 cm in length and 2.5 mm in diameter, N144A in color, raceme starts at 3 cm from base.

*Pedicels.*—Average 6 mm in length and 0.8 mm in diameter, 138B in color.

*Bracts.*—1 per pedicel, lanceolate in shape, average of 4.5 mm in length and 2.5 mm in width, glabrous on upper and lower surface, entire margin, narrowly acute apex, broadly cuneate base.

*Petals.*—6, arranged in 2 whorls of 3, un-fused, obovate in shape, upper and lower surface is glabrous, entire margin, cuneate base, deeply retuse apex, about 6 mm in length and 2 mm in width, color is 3B on lower and upper surface, curved inward.

*Calyx.*—Composed of 2 whorls of 3 petaloid sepals.

*Sepals.*—6 (3 inner and 3 outer), oval to elliptic in shape, 3A in color, glabrous inner and outer surface, outer surface is 4 mm in length and 3 mm in width, inner surface is 6 mm in length and 3.5 mm in width, entire margin, broadly acute apex and cuneate base.

Reproductive organs:

*Gynoecium.*—1 pistil, about 3 mm in length and 1 mm in width, style 1 mm in length and 1.2 mm in width and 138C in color, single peltate stigma is 138C in color, ovary superior, 1 mm in diameter and 2 mm in length, 138C in color.

*Androcoecium.*—6 stamens, un-fused but curved next to inner surface of petals, filaments are 151C in color, about 4 mm in length and 0.8 mm, anthers are 151C in color and open by 2 valves about 0.5 mm in diameter, pollen was moderately abundant, 138C in color but glistening or crystal-like in appearance.

*Fruit and seed.*—Berry, ovoid in shape, about 1 cm in length and 6 mm in width, pruinose surface, and 98A in color, are obovate in shape, about 6 mm in length and 3.5 mm in width and a blend of N199A and 147A in color.

It is claimed:

1. A new and distinct cultivar of *Mahonia* hybrid plant named 'Marvel' as herein illustrated and described.

* * * * *